US00PP34571P3

(12) United States Plant Patent
Post

(10) Patent No.: US PP34,571 P3
(45) Date of Patent: Sep. 13, 2022

(54) ***CHRYSANTHEMUM* PLANT NAMED 'DLFROC2'**

(50) Latin Name: ***Chrysanthemum* X *morifolium***
Varietal Denomination: 'DLFROC2'

(71) Applicant: Arie Gerard Post, Delft (NL)

(72) Inventor: Arie Gerard Post, Delft (NL)

(73) Assignee: DELIFLOR ROYALTIES B.V., Maasdijk (NL)

( * ) Notice: Subject to any disclaimer, the term of this patent is extended or adjusted under 35 U.S.C. 154(b) by 0 days.

(21) Appl. No.: 17/502,988

(22) Filed: Oct. 15, 2021

(65) Prior Publication Data

US 2022/0124953 P1 Apr. 21, 2022

Related U.S. Application Data

(60) Provisional application No. 63/093,198, filed on Oct. 17, 2020.

(51) Int. Cl.
*A01H 5/02* (2018.01)
*A01H 6/14* (2018.01)

(52) U.S. Cl.
USPC ..... Plt./289
CPC ..... *A01H 6/1424* (2018.05)

(58) Field of Classification Search
USPC ..... Plt./289
CPC ..... A01H 6/1424; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Chrysanthemum* plant named 'DLFROC2', characterized by its upright plant habit; uniform growth habit; dark green-colored leaves; rapid, uniform and freely flowering habit; strong upright flowering stems; decorative-type inflorescences with bright yellow-colored ray florets; and good postproduction longevity.

1 Drawing Sheet

Figure 1:
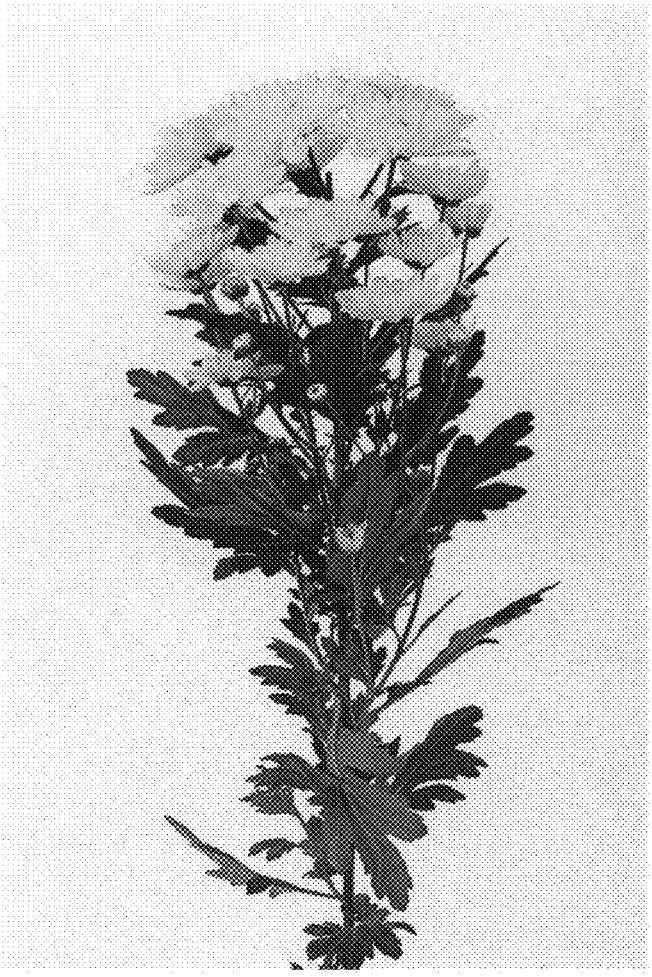

Botanical designation: *Chrysanthemum* X *morifolium*.
Cultivar denomination: 'DLFROC2'.

STATEMENT REGARDING PRIOR DISCLOSURES BY INVENTOR/APPLICANT & ASSIGNEE

An European Plant Breeders' Rights application for the instant plant was filed by the Assignee, Deliflor Royalties B.V. of Maasdijk, The Netherlands on Mar. 19, 2020, application number 2020/0782. Foreign priority is not claimed to this application.

A Japanese Plant Breeders' Rights application for the instant plant was filed by the Assignee, Deliflor Royalties B.V. of Maasdijk, The Netherlands on Jul. 30, 2020, application number 34846. Foreign priority is not claimed to this application.

A Malaysian Plant Breeders' Rights application for the instant plant was filed by the Assignee, Deliflor Royalties B.V. of Maasdijk, The Netherlands on Sep. 29, 2020, application number PVBT 049/20. Foreign priority is not claimed to this application.

A Vietnamese Plant Breeders' Rights application for the instant plant was filed by the Assignee, Deliflor Royalties B.V. of Maasdijk, The Netherlands on Oct. 16, 2020, application number 2020_170. Foreign priority is not claimed to this application.

A Colombian Plant Breeders' Rights application for the instant plant was filed by the Assignee, Deliflor Royalties B.V. of Maasdijk, The Netherlands on Dec. 29, 2020, application number A202741. Foreign priority is not claimed to this application.

A Chinese Plant Breeders' Rights application for the instant plant was filed by the Assignee, Deliflor Royalties B.V. of Maasdijk, The Netherlands on Mar. 2, 2021, application number 20211001376. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Chrysanthemum* plant, botanically known as *Chrysanthemum* x *morifolium*, typically grown as a cut flower *Chrysanthemum* and hereinafter referred to by the name 'DLFROC2'.

The new *Chrysanthemum* plant is a product of a planned breeding program conducted by the Inventor in Maasdijk, The Netherlands. The objective of the breeding program is to create new cut flower *Chrysanthemum* plants with numerous attractive inflorescences.

The new *Chrysanthemum* plant is a naturally-occurring whole plant mutation of *Chrysanthemum* x *morifolium* 'Delibaltica', not patented. The new *Chrysanthemum* plant was discovered and selected as a single flowering plant from within a population of plants of 'Delibaltica' in a controlled greenhouse environment in Maasdijk, The Netherlands in June, 2015.

Asexual reproduction of the new *Chrysanthemum* plant by vegetative terminal cuttings since June, 2015 in a controlled greenhouse environment in Maasdijk, The Netherlands, has shown that the unique features of this new *Chrysanthemum* plant are stable and reproduced true to type in successive generations of asexual reproduction.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'DLFROC2'. These characteristics in combination distinguish 'DLFROC2' as a new and distinct *Chrysanthemum* plant:

1. Upright plant habit; uniform growth habit.
2. Dark green-colored leaves.
3. Rapid, uniform and freely flowering habit.
4. Strong upright flowering stems.
5. Decorative-type inflorescences with bright yellow-colored ray florets.
6. Good postproduction longevity.

Plants of the new *Chrysanthemum* differ primarily from plants of the mutation parent, 'Delibaltica' in ray floret color as ray florets of plants of the new *Chrysanthemum* are bright yellow in color whereas ray florets of plants of 'Delibaltica' are white in color.

Plants of the new *Chrysanthemum* can be compared to plants of *Chrysanthemum* X *morifolium* 'Delibaltica Yellow', not patented. In side-by-side comparisons, plants of the new *Chrysanthemum* differ primarily from plants of 'Delibaltica Yellow' in response time as plants of the new *Chrysanthemum* flower about one week earlier than plants of 'Delibaltica Yellow'. In addition, inflorescences of plants of the new *Chrysanthemum* are smaller than inflorescences of 'Delibaltica Yellow'.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type.

The photograph at the top of the sheet (FIG. 1) comprises a side perspective view of a typical flowering stem of 'DLFROC2' grown as a spray-type cut flower.

Figure 2:
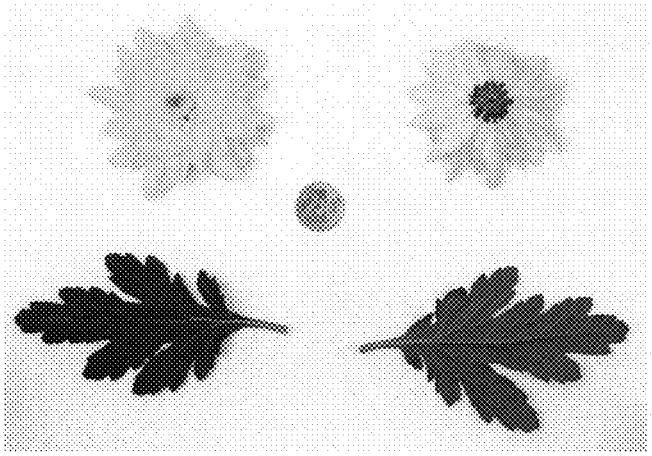

The photograph at the bottom of the sheet (FIG. 2) is a close-up view of upper (left) and lower (right) surfaces of typical inflorescences (top of figure) and typical leaves (bottom of figure) of 'DLFROC2'.

DETAILED BOTANICAL DESCRIPTION

The aforementioned photographs and following observations and measurements describe plants grown during the autumn in ground beds in a glass-covered greenhouse in Maasdijk, The Netherlands and under cultural practices typical of commercial cut *Chrysanthemum* production. Plants were initially given long day/short night treatments followed by short day/long night treatments to induce flower initiation and development. During the production of the plants, day temperatures ranged from 18° C. to 25° C., night temperatures ranged from 20° C. to 22° C. and light levels averaged 8 klux. Plants were grown as single-stem spray-type plants and were nine weeks old when the photographs and the description were taken. In the following description, color references are made to The Royal Horticultural Society Colour Chart, 2015 Edition, except where general terms of ordinary dictionary significance are used.

Botanical classification: *Chrysanthemum* X *morifolium* 'DLFROC2'.

Parentage: Naturally-occurring whole plant mutation of *Chrysanthemum* x *morifolium* 'Delibaltica', not patented.

Propagation:

*Type*.—Terminal vegetative cuttings.

*Time to initiate roots, summer*.—About four days at temperatures about 20° C.

*Time to initiate roots, winter*.—About six days at temperatures about 20° C.

*Time to produce a rooted young plant, summer*.—About 13 days at temperatures about 20° C.

*Time to produce a rooted young plant, winter*.—About 15 days at temperatures about 20° C.

*Root description*.—Fine, fibrous; typically light brown in color, actual color of the roots is dependent on substrate composition, water quality, fertilizers, substrate temperature and physiological age of roots.

*Rooting habit*.—Freely branching, medium density.

Plant description:

*Plant and growth habit*.—Herbaceous decorative-type cut flower that is typically grown as a single stem spray-type; upright plant habit; vigorous growth habit and rapid growth rate.

*Plant height, soil level to top of foliar plane*.—About 72.2 cm.

*Plant height, soil level to top of inflorescence plane*.—About 77.4 cm.

*Plant (spray) diameter*.—About 24.7 cm.

*Flowering stem length*.—About 68 cm.

*Flowering stem diameter*.—About 7 mm.

*Flowering stem internode length*.—About 2.7 cm.

*Flowering stem strength*.—Strong.

*Flowering stem aspect*.—Erect.

*Flowering stem texture and luster*.—Moderately pubescent; slightly glossy.

*Flowering stem color, developing*.—Close to 143A.

*Flowering stem color, developed*.—Close to 146A and 147C.

*Leaf description*.—Arrangement: Alternate; simple. Length: About 12.6 cm. Width: About 7.6 cm. Shape, in overall outline: Obovate to broadly elliptic. Apex: Abruptly acute, minute. Base: Attenuate. Margin: Palmately lobed, coarsely dentate to serrate; sinuses parallel to slightly divergent and medium in depth to deep. Texture and luster, upper surface: Moderately to densely pubescent, not rugose; slightly velvety; slightly glossy. Texture and luster, lower surface: Moderately to densely pubescent, prominent venation; slightly glossy. Venation pattern: Pinnate, reticulate. Color: Developing and fully developed leaves, upper surface: Close to between NN137A and 139A; venation, close to 146A. Developing and fully developed leaves, lower surface: Close to 147B; venation, close to 146B. Petioles: Length: About 2.1 cm. Diameter: About 3 mm by 4 mm. Strength: Moderately strong. Texture and luster, upper surface: Densely pubescent; slightly glossy. Texture and luster, lower surface: Moderately pubescent; slightly glossy. Color, upper surface: Close to 146B; edges, close to NN137B. Color, lower surface: Close to 147B; edges, close to 137B. Stipules: Quantity, appearance and arrangement: Two leafy stipules, opposite, at the petiole attachment to the stem. Length: About 9 mm. Width: About 1 cm. Shape, in overall outline: Roughly reniform. Texture and luster, upper surface: Densely pubescent; slightly glossy. Texture and luster, lower surface: Moderately pubescent; slightly glossy. Color, upper surface: Close to 146B. Color, lower surface: Close to 147B.

Inflorescence description:

*Appearance*.—Decorative-type inflorescence form with obovate-shaped ray florets and tubular disc florets; inflorescences borne perpendicular to peduncles and face mostly upright; ray and disc florets develop acropetally on a capitulum.

*Fragrance*.—Faintly fragrant; typical of *Chrysanthemums*.

*Flowering response*.—Under natural conditions, plant flower in the autumn/winter in the Northern Hemisphere; at other times of the year, inflorescence initiation and development can be induced under short day/long night conditions (at least 13.5 hours of darkness); uniform flowering habit and short response time, plants exposed to two weeks of long day/short night conditions after planting followed by photoinductive short day/long night conditions flower about 51 days later when grown as a spray-type.

*Postproduction longevity*.—Good postproduction longevity; after a seven-day storage period, cut flowers will maintain good color and substance for about two weeks in an interior environment; inflorescences persistent.

*Quantity of inflorescences*.—Typically grown as a spray-type, about 22 inflorescences develop per flowering stem.

*Inflorescence size*.—Diameter, grown as a spray-type: About 8.6 cm. Depth (height), grown as a spray-type: About 3 cm. Disc diameter, grown as a spray-type: If disc florets are present, about 1 mm; inconspicuous.

*Receptacles*.—Height: About 3 mm. Diameter: About 5 mm. Shape: Flattened globular. Color: Close to 145B.

*Inflorescence buds*.—Height: About 1 cm. Diameter: About 1.2 cm. Shape: Flattened spherical. Texture and luster: Sparsely pubescent; slightly glossy. Color: Developing involucral bracts, close to 137B and 138C; developing ray florets, close to 4B and 4C.

*Ray florets*.—Quantity and arrangement: About 200 arranged in about eight whorls. Length: About 2.9 cm, varying between 0.9 cm and 4.5 cm. Width: About 1 cm, varying between 0.1 cm and 1.8 mm. Shape: Obovate; moderately convex, moderately carinate. Apex: Shallowly praemorse to shallowly emarginate. Base: Cuneate. Margin: Entire; not undulate. Aspect: About 20° to 90° from vertical. Texture and luster, upper surface: Smooth, glabrous; moderately velvety; matte. Texture and luster, lower surface: Smooth, glabrous; slightly velvety; slightly glossy. Color: When opening, upper surface: Close to 4A. When opening, lower surface: Close to 5D; distally, close to 4B. Fully opened, upper surface: Close to 4B; distally, close to 4A; venation, close to 4B and 4A; color does not change with subsequent development. Fully opened, lower surface: Close to 4C; distally, close to 4B; venation, close to 4C and 4B; color does not change with subsequent development.

*Disc florets*.—Quantity and arrangement: If present, about one or two at the center of the receptacle. Length: About 5 mm. Diameter: About 1 mm. Shape: Lower 80% fused into a tube; upper 20% free. Apex: Acute. Margin, free-part: Entire. Texture and luster, inner and outer surfaces: Smooth, glabrous; glossy. Color, when opening, inner and outer surfaces: Apex: Close to N144C. Mid-section and base: Close to 157D. Color, fully opened, inner and outer surfaces: Apex: Close to 150C. Mid-section and base: Close to 157D.

*Involucral bracts*.—Quantity and arrangement: About 26 arranged in about two whorls. Length: About 1.1 cm. Width: About 3 mm. Shape: Oblong. Apex: Obtuse. Base: Cuneate. Margin: Entire. Texture and luster, upper surface: Smooth, glabrous; glossy. Texture and luster, lower surface: Sparsely pubescent; matte. Color, upper surface: Close to 144A; lateral margins, translucent and close to 145D and 157A and apical margins tinged with close to N199A. Color, lower surface: Close to 137B and NN137A; lateral margins, translucent and close to 145D and 157A and apical margins tinged with close to N199A.

*Peduncles*.—Length, terminal peduncle: About 4.6 cm. Diameter, terminal peduncle: About 3.5 mm. Length, third peduncle: About 7.1 cm. Diameter, third peduncle: About 3 mm. Strength: Strong. Aspect, terminal peduncle: Upright. Aspect, third peduncle: About 50° from the flowering stem axis. Texture and luster: Moderately pubescent; moderately glossy. Color: Close to slightly darker than 143A.

*Reproductive organs*.—Androecium: Present on disc florets only. Quantity: About five per floret. Filament length: About 2 mm. Filament color: Close to 145D. Anther size: About 0.5 mm by 1.75 mm. Anther shape: Oblong. Anther color: Close to 151C. Pollen amount: Scarce. Pollen color: Close to 17A. Gynoecium: Present on both ray and disc florets. Quantity: One per floret. Pistil length: About 5 mm. Style length: About 4 mm. Style color: Close to 145A. Stigma diameter: About 1 mm. Stigma shape: Cleft to three-parted, decurrent. Stigma color: Close to 145B. Ovary color: Close to 157A.

*Seeds and fruits*.—To date, seed and fruit production have not been observed on plants of the new *Chrysanthemum*.

Pathogen & pest resistance: Plants of the new *Chrysanthemum* have been observed to be resistant to *Fusarium* Wilt (*Fusarium oxysporum* spp. *chrysanthemi* (strain FoNL1)). To date, plants of the new *Chrysanthemum* have not been observed to be resistant to pests and other pathogens common to *Chrysanthemum* plants grown under commercial conditions.

Temperature tolerance: Plants of the new *Chrysanthemum* have been observed to tolerate temperatures ranging from about −12° C. to 35° C. and to be suitable for USDA Hardiness Zones 8 to 10.

It is claimed:

1. A new and distinct *Chrysanthemum* plant named 'DLFROC2' as illustrated and described.

* * * * *